(12) United States Patent
Waller et al.

(10) Patent No.: US 10,898,658 B2
(45) Date of Patent: Jan. 26, 2021

(54) COMPACT INJECTION DEVICE WITH TELESCOPING COMPONENTS

(71) Applicant: LynJohnston, LLC, Kalispell, MT (US)

(72) Inventors: Linda J. Waller, Kalispell, MT (US); Paul Henninge, Burlington, VT (US)

(73) Assignee: LynJohnston, LLC, Kalispell, MT (US)

( * ) Notice: Subject to any disclaimer, the term of this patent is extended or adjusted under 35 U.S.C. 154(b) by 577 days.

(21) Appl. No.: 15/642,283

(22) Filed: Jul. 5, 2017

(65) Prior Publication Data

US 2018/0028765 A1 Feb. 1, 2018

Related U.S. Application Data

(60) Provisional application No. 62/358,645, filed on Jul. 6, 2016.

(51) Int. Cl.
| | |
|---|---|
| *A61M 5/46* | (2006.01) |
| *A61M 5/20* | (2006.01) |
| *A61M 5/315* | (2006.01) |
| *A61M 5/32* | (2006.01) |

(52) U.S. Cl.
CPC .............. *A61M 5/46* (2013.01); *A61M 5/20* (2013.01); *A61M 5/2033* (2013.01); *A61M 5/31511* (2013.01); *A61M 5/3202* (2013.01); *A61M 2005/31518* (2013.01); *A61M 2209/088* (2013.01)

(58) Field of Classification Search
CPC .......... A61M 2005/31518; A61M 5/46; A61M 2005/2073
See application file for complete search history.

(56) References Cited

U.S. PATENT DOCUMENTS

| | | | |
|---|---|---|---|
| 1,436,707 A | 11/1922 | Gaschke | |
| 2,833,280 A * | 5/1958 | Hein, Jr. | ............ A61M 5/31511 604/89 |
| 3,605,744 A | 9/1971 | Dwyer | |
| 3,783,997 A | 1/1974 | Brown | |
| 3,820,652 A | 6/1974 | Thackston | |

(Continued)

FOREIGN PATENT DOCUMENTS

| | | |
|---|---|---|
| WO | WO-2009/017277 A1 | 2/2009 |
| WO | WO-2010/033782 A2 | 3/2010 |

(Continued)

*Primary Examiner* — Emily L Schmidt
(74) *Attorney, Agent, or Firm* — Dorsey & Whitney LLP

(57) ABSTRACT

An injection device uses telescoping and/or nested components and other features to make the overall device compact in size. The device is configured to have a storage position and an extended position, such that its needle is positioned within the housing of the device in a storage position, with the needle extending beyond the device housing when needed for an injection. The telescoping plunger mechanism has a storage position and an extended position for use. The device includes a needle depth cover, which extends from the device housing for use, and guides the user as to the correct depth for the needle to penetrate the user's skin. A switch allows different depth settings, for example allowing a deeper penetration for injection into a leg, and shallower penetration for injection into an arm.

66 Claims, 11 Drawing Sheets

(56) References Cited

U.S. PATENT DOCUMENTS

| | | |
|---|---|---|
| 3,841,329 A | 10/1974 | Killinger |
| 3,916,893 A | 11/1975 | De Felice |
| 4,011,868 A | 3/1977 | Friend |
| 4,221,218 A | 9/1980 | Pfleger |
| 4,493,704 A | 1/1985 | Beard et al. |
| 4,581,023 A | 4/1986 | Kuntz |
| 4,583,973 A | 4/1986 | Humphrey et al. |
| 4,601,708 A | 7/1986 | Jordan |
| 4,710,171 A | 12/1987 | Rosenberg |
| 4,863,433 A * | 9/1989 | Payne .................. A61M 5/002 604/194 |
| 5,048,684 A | 9/1991 | Scott |
| 5,141,496 A | 8/1992 | Dalto et al. |
| 5,873,856 A | 2/1999 | Hjertman et al. |
| 5,876,380 A | 3/1999 | Manganini et al. |
| 6,213,977 B1 | 4/2001 | Hjertman et al. |
| 7,011,649 B2 | 3/2006 | De La Serna et al. |
| 7,931,618 B2 | 4/2011 | Wyrick |
| 8,337,472 B2 | 12/2012 | Edginton et al. |
| 8,535,278 B2 | 9/2013 | Mudd |
| 8,597,245 B2 | 12/2013 | Jeter et al. |
| 8,636,702 B2 | 1/2014 | Schiller et al. |
| 8,647,303 B2 | 2/2014 | Cowe |
| 8,657,793 B2 | 2/2014 | Pellegrini et al. |
| 8,882,719 B2 | 11/2014 | Manke et al. |
| 9,078,974 B2 | 7/2015 | Manke et al. |
| 9,078,975 B2 | 7/2015 | Manke et al. |
| 9,101,719 B2 | 8/2015 | Vernizeau et al. |
| 9,144,446 B2 | 9/2015 | Bogert et al. |
| 9,220,843 B2 | 12/2015 | Mudd |
| 9,333,146 B2 | 5/2016 | Perot et al. |
| 9,333,288 B2 | 5/2016 | Hilliard et al. |
| 9,339,606 B2 | 5/2016 | Evans et al. |
| 9,440,026 B2 | 9/2016 | Wozencroft |
| D772,409 S | 11/2016 | Buell et al. |
| 9,629,961 B2 | 4/2017 | Manke et al. |
| D787,673 S | 5/2017 | Buell et al. |
| 9,681,889 B1 | 6/2017 | Greenhalgh et al. |
| 9,724,660 B2 | 8/2017 | Bogert et al. |
| 2006/0178641 A1 | 8/2006 | Reynolds |
| 2006/0229568 A1 | 10/2006 | Koopman |
| 2007/0060885 A1 * | 3/2007 | Wu ....................... A61M 5/322 604/110 |
| 2009/0318880 A1 | 12/2009 | Janish |
| 2010/0191184 A1 | 7/2010 | Choi |
| 2010/0280410 A1 | 11/2010 | Moos et al. |
| 2012/0226233 A1 * | 9/2012 | Schraga ............. A61M 5/3205 604/111 |
| 2013/0085457 A1 * | 4/2013 | Schiff ................ A61M 5/31511 604/228 |
| 2015/0088067 A1 | 3/2015 | Limaye et al. |
| 2017/0182254 A1 | 6/2017 | Heinsbergen et al. |

FOREIGN PATENT DOCUMENTS

| | | |
|---|---|---|
| WO | WO-2010/033782 A3 | 3/2010 |
| WO | WO-2015/117131 A1 | 8/2015 |

* cited by examiner

COMPACT INJECTION DEVICE WITH TELESCOPING COMPONENTS

CROSS-REFERENCE TO RELATED APPLICATION

This application claims the benefit of U.S. Provisional Application No. 62/358,645, filed Jul. 6, 2016

FEDERALLY-SPONSORED RESEARCH

None

BACKGROUND

The present application relates to the field of injection devices such as syringes, as used for injections of medications.

BRIEF SUMMARY

The injection device described herein uses telescoping and/or nested components and other features in order to make the overall device compact in size. The compact design allows the device to be easily carried or worn by a person, such as in the form of a bracelet or pendant. The device is configured to have a storage position and an extended position, such that its needle is positioned within the housing of the device in a storage position, with the needle extending beyond the device housing when needed for an injection. The telescoping plunger mechanism also has a storage position and an extended position for use. The device includes a needle depth cover, which extends from the device housing for use, and guides the user as to the correct depth for the needle to penetrate the user's skin. A switch allows different depth settings, for example allowing a deeper penetration for injection into a leg, and shallower penetration for injection into an arm.

In an embodiment of the injection device, there is: a main case containing a syringe body; a two-piece telescoping plunger movably engaged within the syringe body, the telescoping plunger including a plunger body and a plunger extension; a tubular needle movably engaged with the syringe body; a medicine volume chamber within the syringe body. The device may expand from a storage position to a deployment position, thereby expanding the telescoping plunger and being capable of delivering the medicine volume chamber's contents through the tubular needle to a body by depressing the telescoping plunger.

In an embodiment of the injection device, there is an injection device, comprising: a syringe body; a two-piece telescoping plunger movably engaged within the syringe body, the telescoping plunger including a plunger body and a plunger extension; a tubular needle movably engaged with the syringe body; a medicine volume chamber within the syringe body; whereby said device may expand from a storage position to a deployment position, thereby expanding the telescoping plunger and being capable of delivering the medicine volume chamber's contents through the tubular needle to a body by depressing the telescoping plunger.

An embodiment of the device may further include a retractable needle depth cover movably engaged with the main case and that surrounds the tubular needle when the tubular needle is in a storage position.

An embodiment of the device may further include a retractable needle depth cover that retracts to a pre-set depth as the tubular needle enters into the body, thereby limiting the needle's penetrative depth into the body, and in which the pre-set depth is controlled by a switch.

An embodiment of the device may further include a pull plug removably engaged with the needle's sharp end, with the pull plug also removably engaged with the main case when the injection device is in the storage position. Removing the pull plug may extend the needle into a deployed position and thereby engage at least one set of needle barbs with at least one set of plug barbs.

An embodiment of the device may further include a switch to control the movement of the device from the storage position to the deployed position.

An embodiment of the device may further include a spring to expand the plunger body relative to the plunger extension.

An embodiment of the device may further include the plunger body and the plunger extension engaged with one another by at least one longitudinal finger and at least one recess when the plunger is in its expanded position.

DETAILED DESCRIPTION

In the preferred embodiment, the medicine contained in the device is epinephrine, as used for emergency treatment of anaphylaxis and/or anaphylactic shock. Those who are afflicted with severe, life-threatening allergies are advised to carry a kit with them at all times that contains a supply of epinephrine and means for injecting said medicine. However, such kits typically are bulky in size, primarily due to the elongated shape of a syringe. The present injection device includes numerous features that allow it to have a compact storage size, while expanding into a deployment position for injection use. Of course, the present injection device is not limited to delivering epinephrine, but can be used for any suitable injectable medicine.

Figure 1:
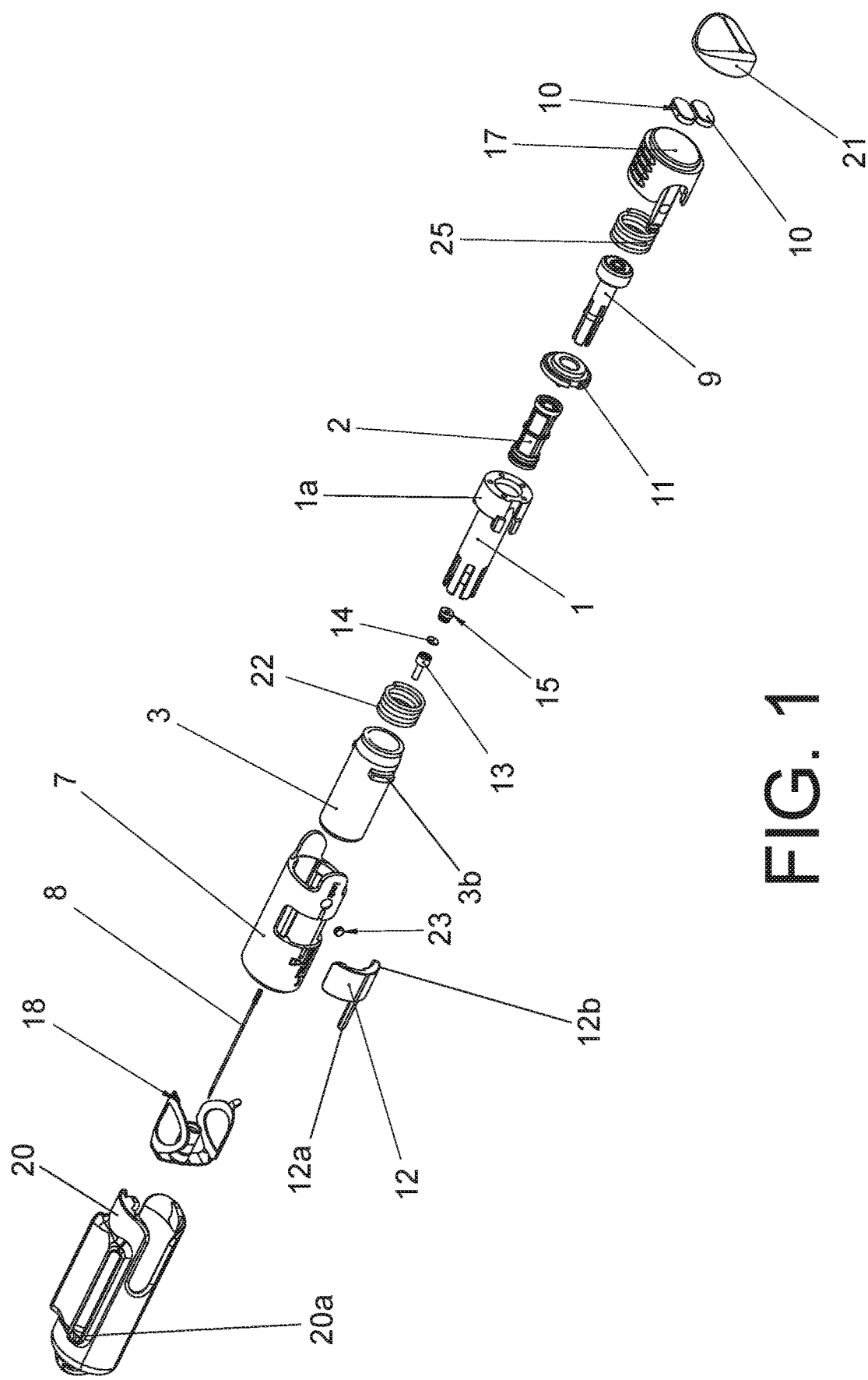
FIG. 1 shows an exploded view of an embodiment of the present device
Figure 4:
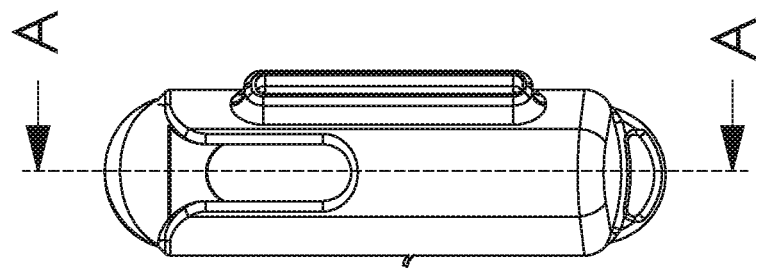
FIG. 4 shows a left side elevation view of an embodiment of the present device
Figure 3:
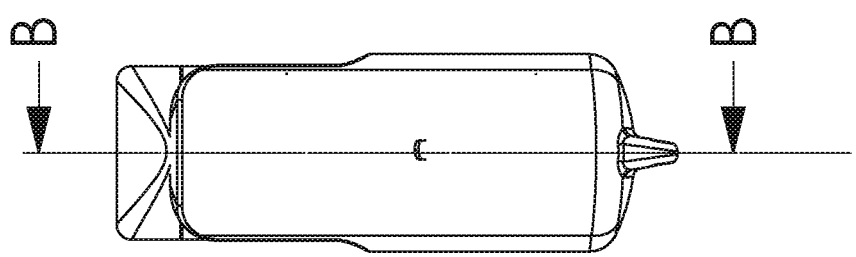
FIG. 3 shows a front elevation view of an embodiment of the present device
Figure 2:
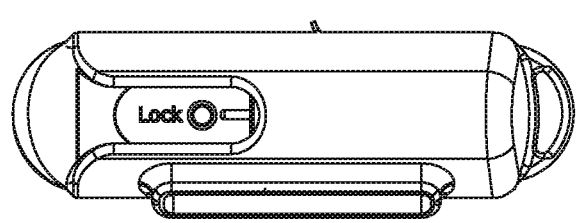
FIG. 2 shows a right side elevation view of an embodiment of the present device

In one embodiment of the device, and in reference to FIG. 1, there is a main case 7. Main case 7 is approximately tubular in shape, with most other components housed within it. Moving inward, needle depth cover 3 is slideably arranged within main case 7, as will be further detailed. For spatial reference throughout this specification, "upper" refers to the plunger end of the overall device, and "lower" refers to the opposing needle end of the device, with "upward" and "downward" similarly referenced.

Figure 5:
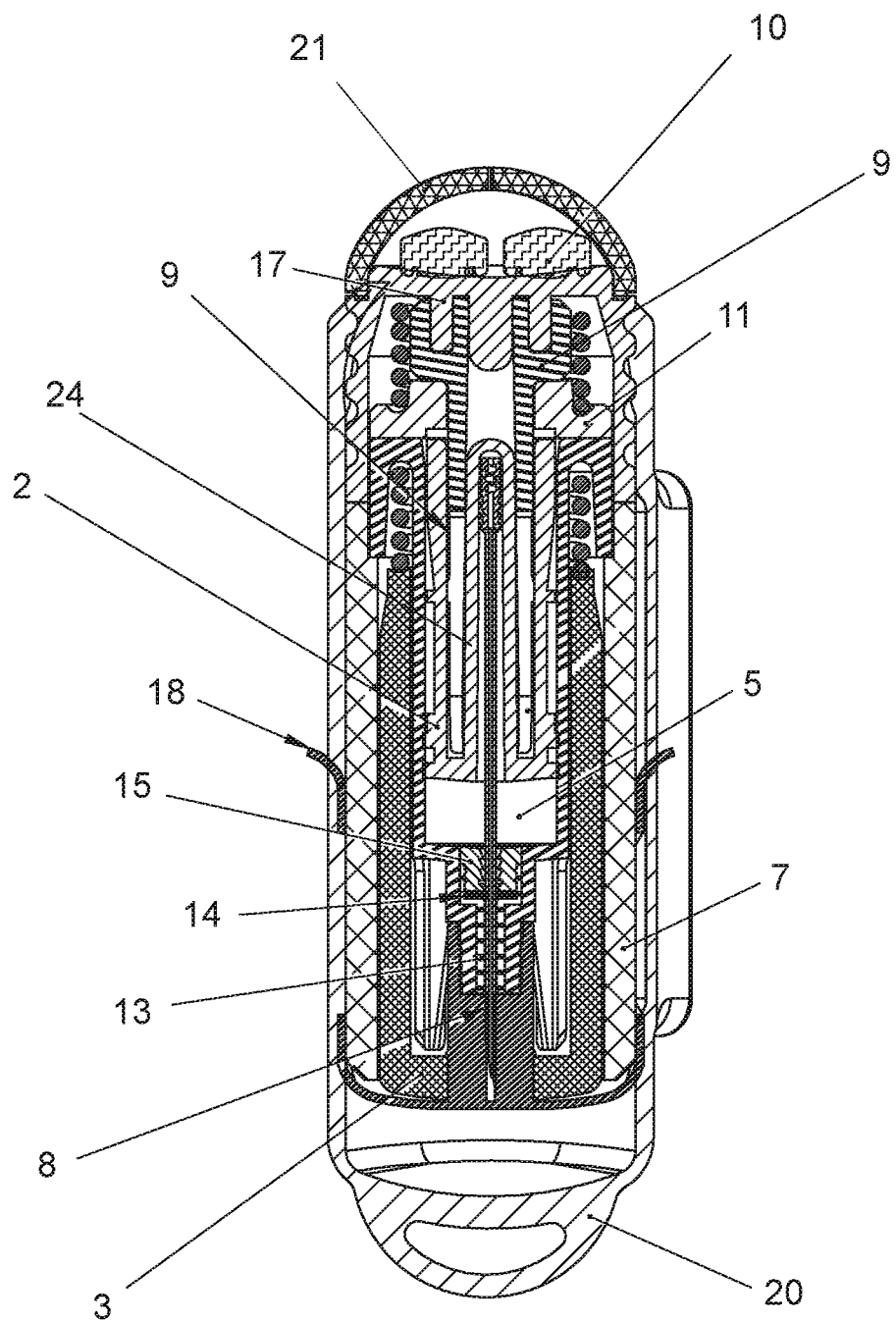
FIG. 5 shows a cross-sectional view of an embodiment of the present device
Figure 6:
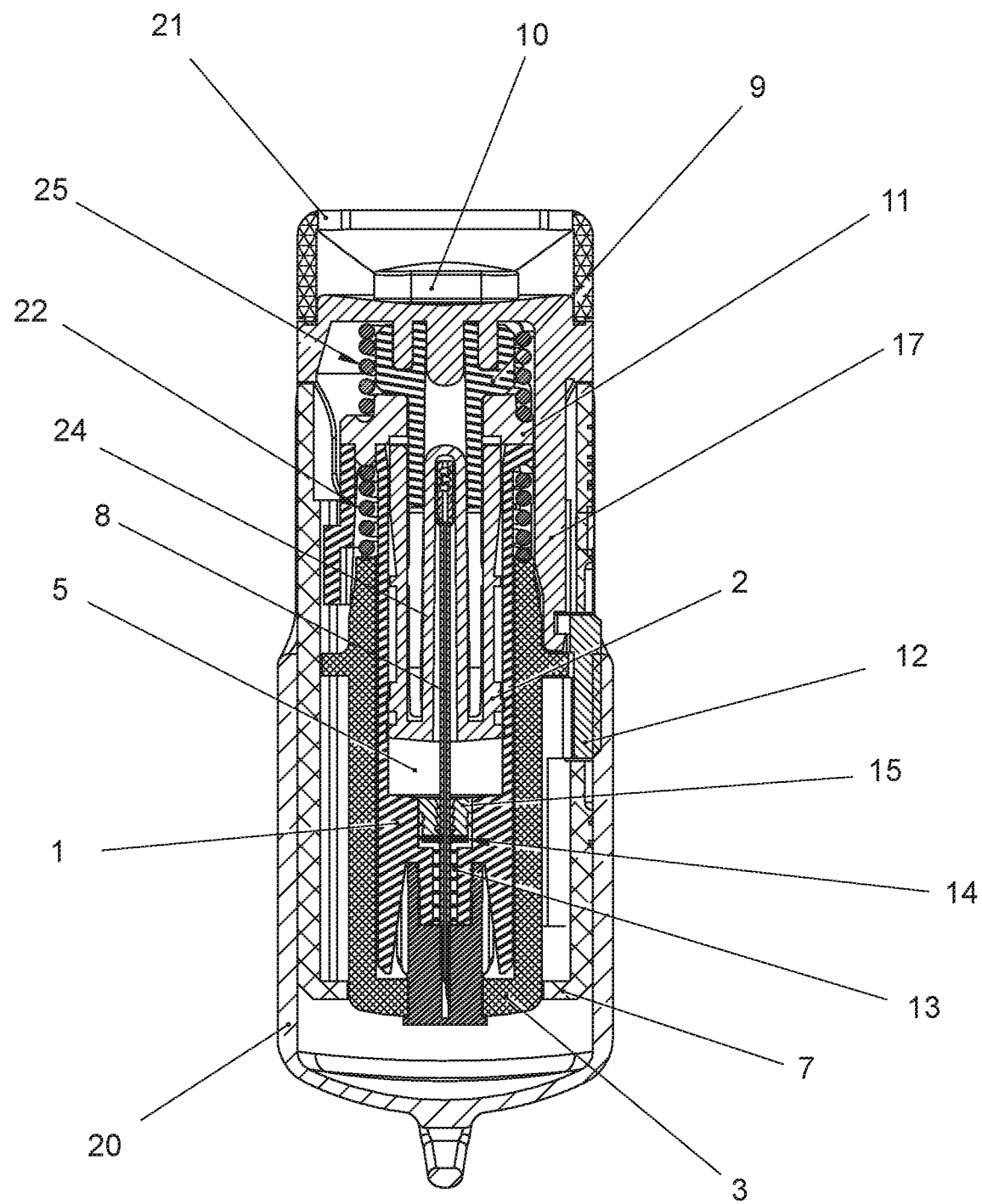
FIG. 6 shows a cross-sectional view of an embodiment of the present device

A needle depth cover return spring 22 is positioned to extend needle depth cover 3 for use, with the lower end of the spring configured to abut the end of depth cover 3. The upper end of spring 22 abuts a flange 1A on a syringe barrel body 1, with a portion of spring 22 surrounding the lower portion of syringe barrel body 1. This spring positioning can be seen in section B-B, FIG. 5, and section A-A, FIG. 6. Tabs 3b on depth cover 3 engage with main case 7, providing a limit to the travel of the cover 3 relative to case 7.

Telescopic syringe plunger body 2, telescopic syringe plunger extension 9, and syringe plunger top 17, together form the full plunger assembly. Retainer 11 engages with barrel body 1 to contain plunger body 2. In FIG. 2-7, the device is shown in its storage position, where syringe plunger extension 9 is positioned inside of syringe plunger body 2, in a telescopic, or nested configuration. That is, the plunger is comprised of concentric tubular sections designed to slide into one another. In deploying the overall device to its extended position for use in injection, syringe plunger extension 9 slides relative to syringe plunger body 2, forming an extended, depressable plunger, as will be further explained.

Figure 15:
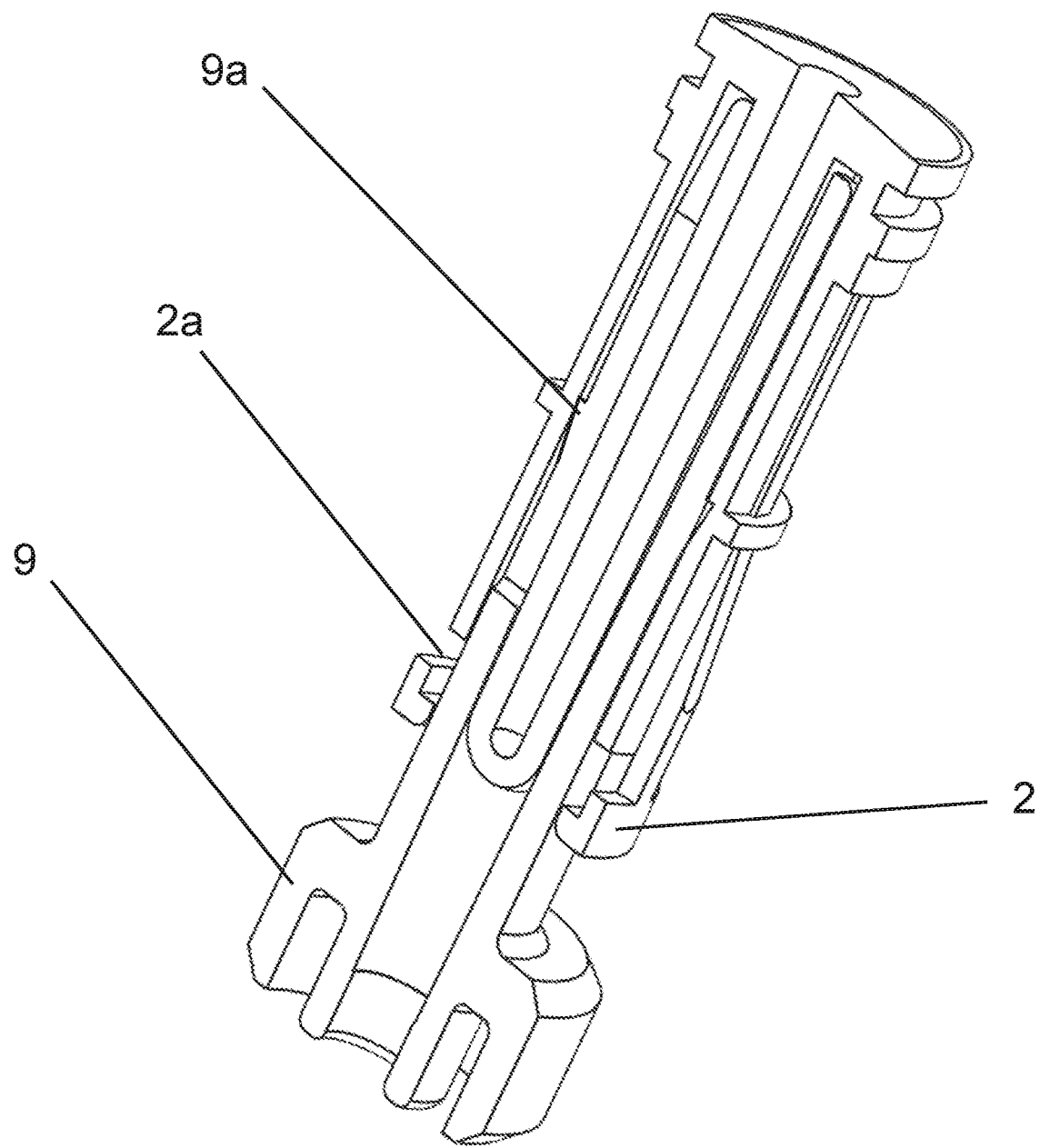
FIG. 15 shows a cross-sectional view of the syringe plunger in its storage position
Figure 16:
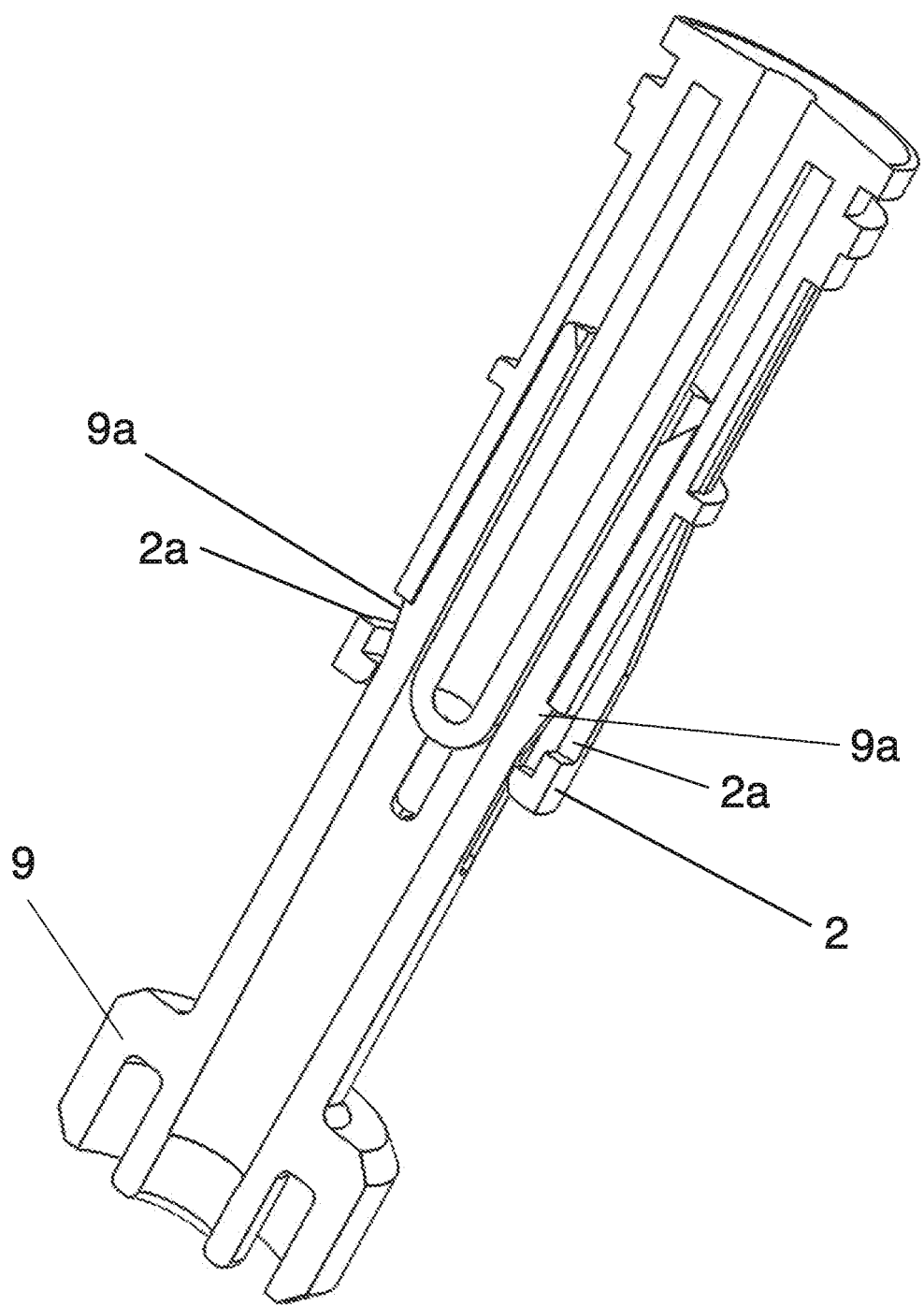
FIG. 16 shows a cross-sectional view of the syringe plunger in its extended position

With reference to FIGS. 15 and 16, the plunger assembly includes the concentric tubular sections of extension 9 and plunger body 2. The primary purpose of such an assembly is to create a plunger which in a storage position is more compact (that is, shorter in overall length) than the length required by the plunger for use in delivering medicine through a needle, as when the device is in an extended position and deployed for use. When switch 12 (as seen in FIG. 1) is moved and allows the device to extend, plunger extension 9 is released with plunger spring 25 causing extension 9 to move upward relative to plunger body 2. Herein, switch 12 includes an element which interlocks with a barb-type element on extension 9, thereby releasing extension 9 under the force of spring 25. Longitudinal fingers 9a, which remain compressed in the storage position, are released outward when spring 25 pushes plunger extension 9 into its final position. Fingers 9a engage in recesses 2a in plunger body 2, thus locking extension 9 in an extended position relative to plunger body 2. Thus, a full length plunger has been configured.

Again in reference to FIG. 1, there is a needle 8, which is a hypodermic type for injection of medicine into a body. As seen in the cross sectional views of FIG. 5 and FIG. 6, which depict the device in its storage position, needle 8 passes through the medicine volume chamber 5. Thus, a mid-portion of the length of needle 8 is positioned within chamber 5, with an upper portion of needle 8 above chamber 5, and a lower portion of needle 8 positioned below chamber 5. As needle 8 is a tubular hypodermic type, this results in the inner passage of needle 8 containing medicine when the device is in its storage position.

Figure 14:
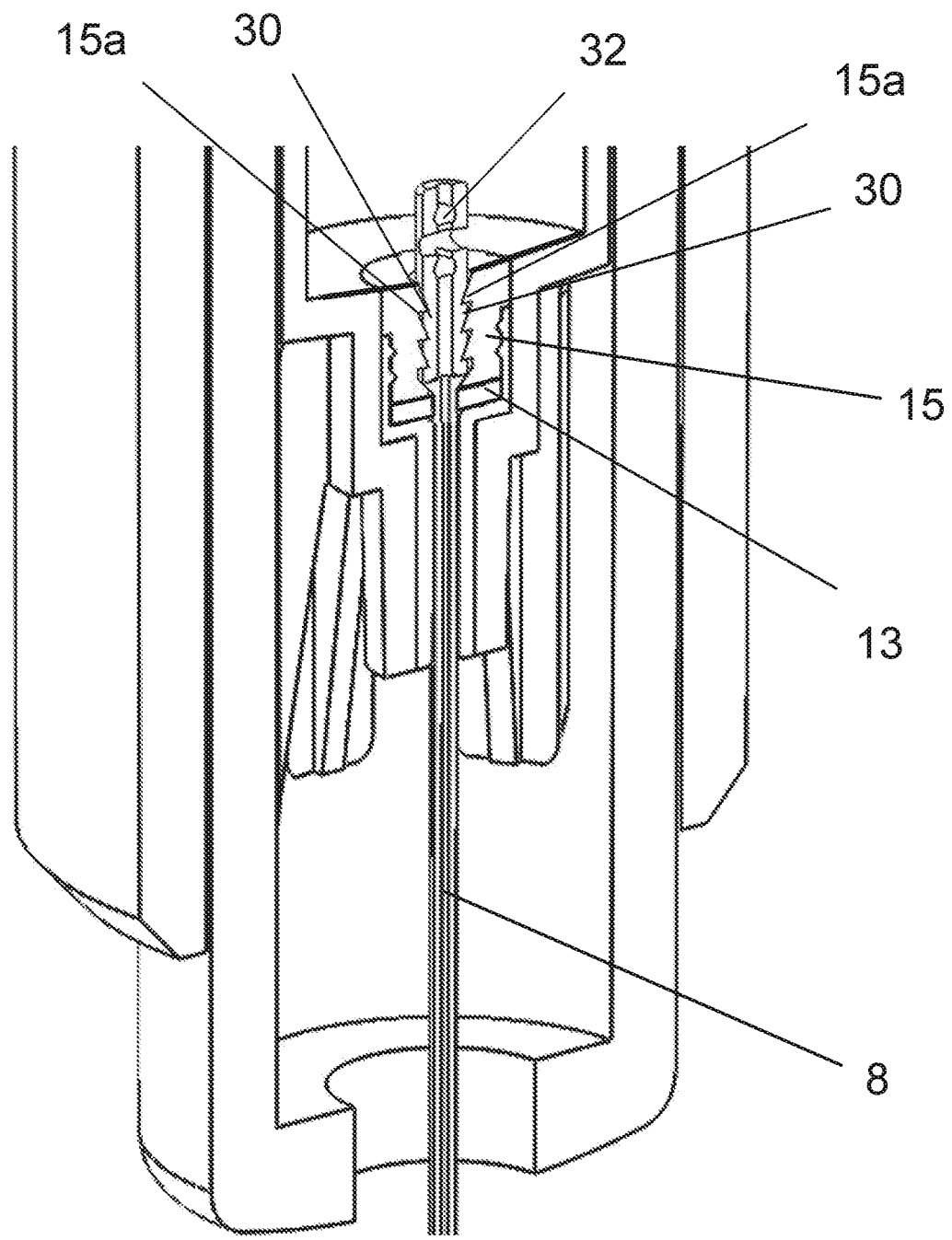
FIG. 14 shows an enlarged view of the needle in its deployed position

In the storage position, the upper portion of needle 8 rests in the inner bore 24 of telescopic syringe plunger body 2, and above chamber 5. Needle 8 is in a retracted, nested position inside telescopic syringe plunger body 2, with the medicine volume contained in the undeployed storage position. The clearance between needle and plunger body 2 is such that a small amount of medicine from chamber 5 may be present inside the bore 24 of body 2 and on the outside of needle 8. Needle 8 contains at least one needle bore opening 32, as shown in FIG. 14, which allow medicine to enter the inner bore of needle 8.

Needle barbs 30 are included on the outer diameter of the upper end of needle 8. When the device deploys from its storage position to its extended position, needle 8 slides downward, with the needle's upper end traveling downward, and needle barbs 30 mate with catch plug barbs 15a, where catch plug barbs 15a are contained in the inner bore of catch plug 15. Catch plug 15 is positioned directly below chamber 5. Thus, as the device is deployed, needle 8 moves downward with the upper end of needle 8 exiting the inside bore of extension 9, until needle barbs 30 (on the OD of the upper end of needle 8) engage with plug barbs 15a, and needle 8 is therefore positioned entirely below chamber 5. FIG. 14 shows an enlarged view of the interlocking barbs of the needle 8 and bushing 13. Bushing 13 is positioned directly below catch plug 15, and together with guide seal 14 align and secure needle 8 within syringe body 1.

Figure 9:
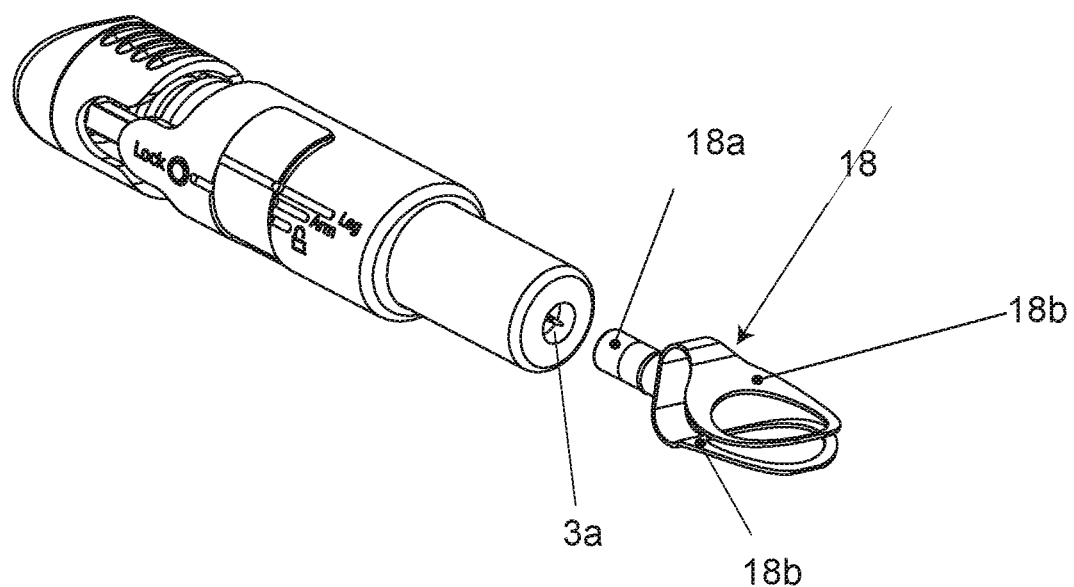
FIG. 9 shows a perspective view of an embodiment of the present device in its deployed position
Figure 10:
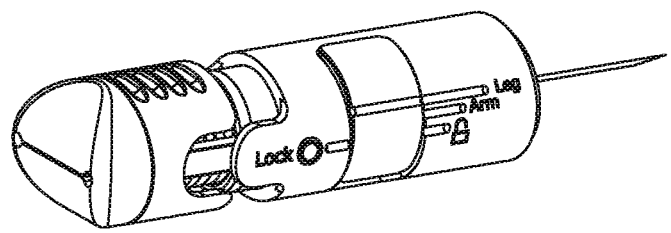
FIG. 10 shows a perspective view of an embodiment of the present device in its deployed position with its needle depth cover compressed, as during an injection
Figure 11:
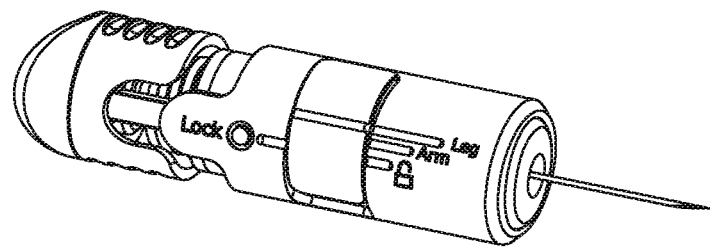
FIG. 11 shows a perspective view of an embodiment of the present device in its deployed position with its needle depth cover compressed, as during an injection
Figure 12:
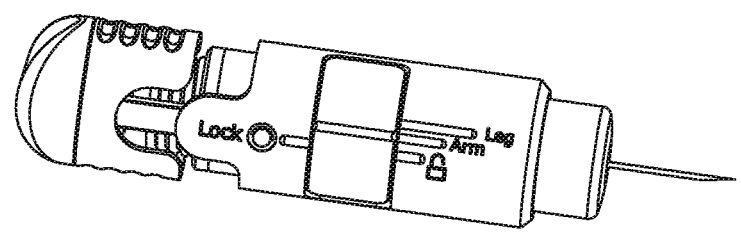
FIG. 12 shows a perspective view of an embodiment of the present device in its deployed position
Figure 13:
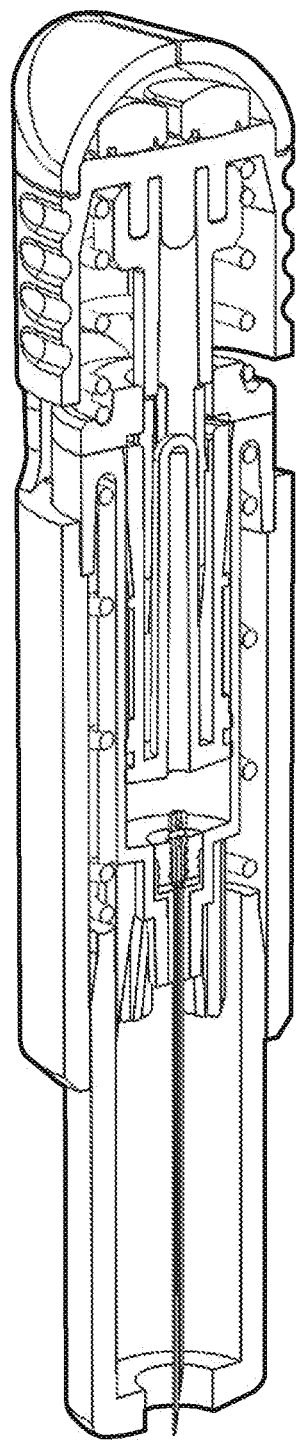
FIG. 13 shows a cross-sectional view of an embodiment of the present device in its deployed position

As the device is deployed, depth cover spring 22, which is in compression when the device is in its storage position, extends depth cover 3 downward, as seen in the deployed view of the device in FIG. 9. Pull plug 18 includes a plug stop 18a, which is removably affixed in cover hole 3a of needle depth cover 3. Plug 18 may be made from a variety of pliable materials, such as various rubber and plastic compounds. Plug stop 18a is removably affixed to the sharp end portion of needle 8, such that when the device deploys and depth cover 3 extends downward, needle 8 travels downward within the overall device, in particular relative to the inside bore of extension 9. Thus, the frictional fit between plug stop 18a and needle 8 is what creates the downward travel of the needle during deployment, providing the required force to engage the interlocking barbs at the top end of the needle.

Creating needle travel as part of device deployment is one of several purposes of needle depth cover 3. A second purpose is that of a depth gauge, such that a user knows how deeply the needle should be inserted into a body. When the device is deployed and ready for injection, the lower end of needle 8 is approximately flush with the front surface of needle depth cover 3. As the needle is inserted into a body, the body presses against the front surface of needle depth cover 3, pushing depth cover 3 upward and compressing spring 22. The needle is inserted to the depth at which need depth cover 3 can no longer be compressed, as determined by the arm/leg depth settings, which will be further explained.

An additional purpose of the needle depth cover 3 is creating a guard around needle 8. When an injection is complete, and the needle is removed from a body, spring 22 causes needle depth cover 3 to again extend downward, covering needle 8, thus providing shielding and protection of the sharp needle end.

Figure 7:
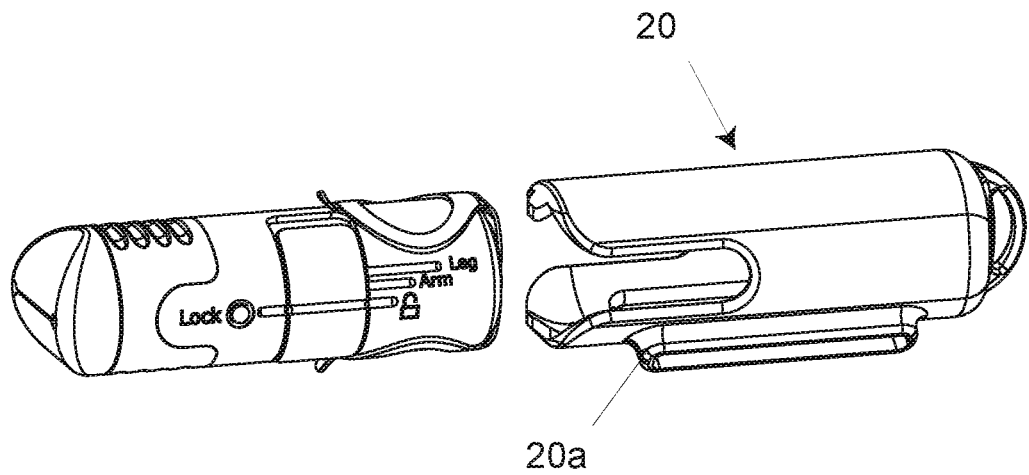
FIG. 7 shows a perspective view of an embodiment of the present device in its storage position
Figure 8:
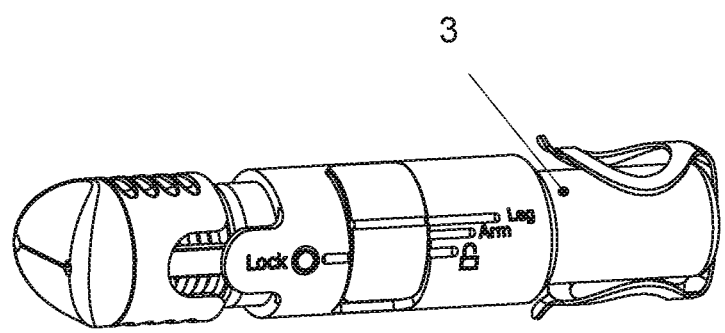
FIG. 8 shows a perspective view of an embodiment of the present device in its deployed position

Plug loops 18b also serve as part of the deployment mechanism. As seen in FIG. 7 and FIG. 8, loops 18b wrap around the device in a low-profile manner when the device is in its storage position. For deployment, loops 18b peel off the device so that that a user's fingers can grasp the loops.

As previously described, plug stop 18a serves in part to pull needle 8 downward within the device as the device moves to its extended position. A user then pulls pull plug 18 off of needle 8; this removal action creates additional tensile force on the needle, which may further seat needle barbs 30 into plug barbs 15a. Pull plug 15 also, of course, shields the lower end of needle 8 during storage.

As seen in FIG. 1, switch 12 serves to unlock the device and release it from its storage position to its extended position. Switch 12 is a mechanical type, and includes tab 12a and flange 12b. Window 23 allows the user to see an indication of the device's position. As the switch is moved from lock position to "arm" or "leg" position, with visual indicators included for such purpose, tab 12a and flange 12b rotate such that they disengage from their mating surface of tab 3a on depth cover 3. The "leg" position of switch 12 allows the needle depth cover 3 to retract further during the insertion of a needle into a body, compared to the arm setting. Thus, the user is guided to a deeper needle penetration for leg use. Of course, the arm and leg depth settings are just examples of depth guides. For instance, depth guides could also be correlated according to use of not just of an injection location, but of the age/size of a user, such as child or adult.

The overall injection device may be configured to be worn by a person, in forms such as but not limited to a wristband, pendant, etc. The length of a traditional syringe makes it impractical to be a worn device, but the compact form of the present device allows practical wearability. FIG. 1 and FIG. 7 show sleeve 20, which houses the overall injection device, and includes slots 20a, into which a wristband or other band can mount. Thus the overall device can be worn as wristband, pendant, etc., and therefore easily carried by those who require immediate access to medicine at all times. The device may include case cap 21 as shown in FIG. 1. Cap 21 is removably attached to syringe plunger top 17, with the enclosed space between creating space for medicine in pill form 10, where the pills may be antihistamines or any other desired drug. This integration allows for the inclusion of a plurality of drug delivery types/forms in a single device.

The following summarizes the overall device in use. The device is removed from sleeve 20. Switch 12 is moved from the position locking the overall device, to a position that causes the device to deploy (such as an "arm" or "leg" setting), with switch mechanisms allowing springs 25 and 22 to expand the device. Needle 8 travels downward, with the user also pulling on pull plug 18, causing needle barbs 30 to mate with catch plug barbs 15a. Syringe plunger extension 9 travels upward, with longitudinal fingers 9a fitting into recesses 2a, thereby forming a full-length plunger. Needle depth cover 3 moves downward under the force of spring 22. Pull plug 18, which engages the sharp end of needle 8, is removed by the user from depth cover 3 and needle 8, revealing the sharp end of needle 8. The device is now ready for injection. The user places the front of needle depth cover 8 against a body and presses downward, until the needle depth cover can depress no further, marking that the needle has entered the body to the correct depth. Plunger 2 is then depressed, forcing medicine through needle 8 and into the body. When the injection is complete, the device is removed from the body, causing depth cover 3 to return to its fully extended position, and thereby shielding the sharp end of needle 8.

Although the present system has been described with respect to one or more embodiments, it will be understood that other embodiments of the present system may be made without departing from the spirit and scope of the present system. Hence, the present system is deemed limited only by claims and the reasonable interpretation thereof.

What is claimed:

1. An injection device, comprising:
   a syringe body;
   a two-piece telescoping plunger movably engaged within the syringe body, the telescoping plunger including a plunger body and a plunger extension;
   a tubular needle movably engaged with the syringe body, wherein the tubular needle is located in the telescoping plunger when the device is in a storage position;
   a medicine volume chamber within the syringe body;
   whereby said device is configured to expand from the storage position to a deployment position, to expand the telescoping plunger, and to deliver a medication in the medicine volume chamber through the tubular needle to a body by depressing the telescoping plunger; and
   wherein a portion of the tubular needle is positioned within the medicine volume chamber when the injection device is in the storage position.

2. The device of claim 1, further comprising a retractable needle depth cover movably engaged with the syringe body and surrounding the tubular needle when the tubular needle is in the storage position.

3. The device of claim 2, in which the retractable needle depth cover is configured to retract to a pre-set depth as the tubular needle enters into the body, thereby limiting the needle's penetrative depth into the body.

4. The device of claim 3, in which the pre-set depth is controlled by a switch.

5. The device of claim 2, in which the depth cover is configured to return to a fully extended position after the device is removed from the body and thereby shield a sharp end of the needle.

6. The device of claim 1, wherein the two-piece telescoping plunger further comprises an inner bore, and the tubular needle resides in the inner bore when the device is in the storage position.

7. The device of claim 6, wherein the inner bore comprises a proximal closed end located inside the syringe body and a distal opening at a distal end of the syringe body.

8. The device of claim 7, wherein the plunger extension is longitudinally slideable between the inner bore and an outer wall of the syringe body.

9. The device of claim 6, further comprising medication in the syringe body.

10. The device of claim 9, wherein a portion of the medication is located in the inner bore and surrounding the needle.

11. The device of claim 1, further comprising a main body, wherein the syringe body is located in the main body.

12. The device of claim 11, further including a pull plug removably engaged with a sharp end of the needle, with the pull plug also removably engaged with the main body when the injection device is in the storage position.

13. The device of claim 12, wherein the pull plug is configured upon removal to extend the needle into a deployed position and thereby engage at least one set of needle barbs with at least one set of plug barbs.

14. The device of claim 1, further comprising a pull plug removably engaged with a sharp end of the needle, with the pull plug also removably engaged with the syringe body when the injection device is in the storage position.

15. The device of claim 14, wherein the pull plug is configured to upon removal to pull the needle into a deployed position and engage at least one set of needle barbs with at least one set of plug barbs.

16. The device of claim 1, further comprising a switch configured to control the movement of the device from the storage position to the deployed position.

17. The device of claim 1, further comprising a spring configured to expand the plunger body relative to the plunger extension.

18. The device of claim 1, in which the plunger body and the plunger extension are engaged with one another by at least one longitudinal finger and at least one recess when the plunger is in its expanded position.

19. An injection device, comprising:
a syringe body;
a two-piece telescoping plunger movably engaged within the syringe body, the telescoping plunger including a plunger body and a plunger extension;
a tubular needle movably engaged with the syringe body, wherein the tubular needle is located in the telescoping plunger when the device is in a storage position;
a medicine volume chamber within the syringe body;
a pull plug removably engaged with a sharp end of the needle, with the pull plug also removably engaged with the syringe body when the injection device is in the storage position, wherein the pull plug is configured to upon removal to pull the needle into a deployed position and engage at least one set of needle barbs with at least one set of plug barbs; whereby said device is configured to expand from the storage position to a deployment position, to expand the telescoping plunger, and to deliver a medication in the medicine volume chamber through the tubular needle to a body by depressing the telescoping plunger.

20. The device of claim 19, further comprising a retractable needle depth cover movably engaged with the syringe body and surrounding the tubular needle when the tubular needle is in the storage position.

21. The device of claim 20, in which the retractable needle depth cover is configured to retract to a pre-set depth as the tubular needle enters into the body, thereby limiting the needle's penetrative depth into the body.

22. The device of claim 21, in which the pre-set depth is controlled by a switch.

23. The device of claim 20, in which the depth cover is configured to return to a fully extended position after the device is removed from the body and thereby shield a sharp end of the needle.

24. The device of claim 20, wherein the two-piece telescoping plunger further comprises an inner bore, and the tubular needle resides in the inner bore when the device is in the storage position.

25. The device of claim 24, wherein the inner bore comprises a proximal closed end located inside the syringe body and a distal opening at a distal end of the syringe body.

26. The device of claim 25, wherein the plunger extension is longitudinally slideable between the inner bore and an outer wall of the syringe body.

27. The device of claim 24, further comprising medication in the syringe body.

28. The device of claim 27, wherein a portion of the medication is located in the inner bore and surrounding the needle.

29. The device of claim 20, further comprising a main body, wherein the syringe body is located in the main body.

30. The device of claim 29, further including a pull plug removably engaged with a sharp end of the needle, with the pull plug also removably engaged with the main body when the injection device is in the storage position.

31. The device of claim 30, wherein the pull plug is configured upon removal to extend the needle into a deployed position and thereby engage at least one set of needle barbs with at least one set of plug barbs.

32. The device of claim 19, further comprising a switch configured to control the movement of the device from the storage position to the deployed position.

33. The device of claim 19, further comprising a spring configured to expand the plunger body relative to the plunger extension.

34. The device of claim 19, in which the plunger body and the plunger extension are engaged with one another by at least one longitudinal finger and at least one recess when the plunger is in its expanded position.

35. The device of claim 19, in which a portion of the tubular needle is positioned within the medicine volume chamber when the injection device is in the storage position.

36. An injection device, comprising:
a syringe body;
a two-piece telescoping plunger movably engaged within the syringe body, the telescoping plunger including a plunger body and a plunger extension;
a tubular needle movably engaged with the syringe body, wherein the tubular needle is located in the telescoping plunger when the device is in a storage position;
a medicine volume chamber within the syringe body;
a retractable needle depth cover movably engaged with the syringe body and surrounding the tubular needle when the tubular needle is in the storage position;
whereby said device is configured to expand from the storage position to a deployment position, to expand the telescoping plunger, and to deliver a medication in the medicine volume chamber through the tubular needle to a body by depressing the telescoping plunger;
wherein the two-piece telescoping plunger further comprises an inner bore, and the tubular needle resides in the inner bore when the device is in the storage position, and wherein the inner bore comprises a proximal closed end located inside the syringe body and a distal opening at a distal end of the syringe body.

37. The device of claim 36, in which the retractable needle depth cover is configured to retract to a pre-set depth as the tubular needle enters into the body, thereby limiting the needle's penetrative depth into the body.

38. The device of claim 37, in which the pre-set depth is controlled by a switch.

39. The device of claim 36, further comprising a pull plug removably engaged with a sharp end of the needle, with the pull plug also removably engaged with the syringe body when the injection device is in the storage position.

40. The device of claim 39, wherein the pull plug is configured to upon removal to pull the needle into a deployed position and engage at least one set of needle barbs with at least one set of plug barbs.

41. The device of claim 36, further comprising a switch configured to control the movement of the device from the storage position to the deployed position.

42. The device of claim 36, further comprising a spring configured to expand the plunger body relative to the plunger extension.

43. The device of claim 36, in which the plunger body and the plunger extension are engaged with one another by at least one longitudinal finger and at least one recess when the plunger is in its expanded position.

44. The device of claim 36, in which a portion of the tubular needle is positioned within the medicine volume chamber when the injection device is in the storage position.

45. The device of claim 36, in which the depth cover is configured to return to a fully extended position after the device is removed from the body and thereby shield a sharp end of the needle.

46. The device of claim 36, wherein the plunger extension is longitudinally slideable between the inner bore and an outer wall of the syringe body.

47. The device of claim 36, further comprising medication in the syringe body.

48. The device of claim 47, wherein a portion of the medication is located in the inner bore and surrounding the needle.

49. The device of claim 36, further comprising a main body, wherein the syringe body is located in the main body.

50. The device of claim 49, further including a pull plug removably engaged with a sharp end of the needle, with the pull plug also removably engaged with the main body when the injection device is in the storage position.

51. The device of claim 50, wherein the pull plug is configured upon removal to extend the needle into a deployed position and thereby engage at least one set of needle barbs with at least one set of plug barbs.

52. An injection device, comprising:
a syringe body;
a main body, wherein the syringe body is located in the main body;
a two-piece telescoping plunger movably engaged within the syringe body, the telescoping plunger including a plunger body and a plunger extension;
a tubular needle movably engaged with the syringe body, wherein the tubular needle is located in the telescoping plunger when the device is in a storage position;
a medicine volume chamber within the syringe body;
a retractable needle depth cover movably engaged with the syringe body and surrounding the tubular needle when the tubular needle is in the storage position;
a pull plug removably engaged with a sharp end of the needle, with the pull plug also removably engaged with the main body when the injection device is in the storage position, wherein the pull plug is configured upon removal to extend the needle into a deployed position and thereby engage at least one set of needle barbs with at least one set of plug barbs;
whereby said device is configured to expand from the storage position to a deployment position, to expand the telescoping plunger, and to deliver a medication in the medicine volume chamber through the tubular needle to a body by depressing the telescoping plunger.

53. The device of claim 52, in which the retractable needle depth cover is configured to retract to a pre-set depth as the tubular needle enters into the body, thereby limiting the needle's penetrative depth into the body.

54. The device of claim 53, in which the pre-set depth is controlled by a switch.

55. The device of claim 52, further comprising a pull plug removably engaged with a sharp end of the needle, with the pull plug also removably engaged with the syringe body when the injection device is in the storage position.

56. The device of claim 55, wherein the pull plug is configured to upon removal to pull the needle into a deployed position and engage at least one set of needle barbs with at least one set of plug barbs.

57. The device of claim 52, further comprising a switch configured to control the movement of the device from the storage position to the deployed position.

58. The device of claim 52, further comprising a spring configured to expand the plunger body relative to the plunger extension.

59. The device of claim 52, in which the plunger body and the plunger extension are engaged with one another by at least one longitudinal finger and at least one recess when the plunger is in its expanded position.

60. The device of claim 52, in which a portion of the tubular needle is positioned within the medicine volume chamber when the injection device is in the storage position.

61. The device of claim 52, in which the depth cover is configured to return to a fully extended position after the device is removed from the body and thereby shield a sharp end of the needle.

62. The device of claim 52, wherein the two-piece telescoping plunger further comprises an inner bore, and the tubular needle resides in the inner bore when the device is in the storage position.

63. The device of claim 62, wherein the inner bore comprises a proximal closed end located inside the syringe body and a distal opening at a distal end of the syringe body.

64. The device of claim 63, wherein the plunger extension is longitudinally slideable between the inner bore and an outer wall of the syringe body.

65. The device of claim 62, further comprising medication in the syringe body.

66. The device of claim 65, wherein a portion of the medication is located in the inner bore and surrounding the needle.

* * * * *